United States Patent [19]

Mixich et al.

[11] Patent Number: 5,656,747
[45] Date of Patent: Aug. 12, 1997

[54] PROCESS FOR THE QUANTITATIVE PURIFICATION OF GLYCOLIPIDS

[75] Inventors: Johann Mixich, Kelkheim; Reinhardt Rothert, Niedernhausen; Dieter Wullbrandt, Hofheim, all of Germany

[73] Assignee: Hoechst Aktiengesellschaft, Frankfurt am Main, Germany

[21] Appl. No.: 145,207

[22] Filed: Nov. 3, 1993

[30] Foreign Application Priority Data

Nov. 15, 1992 [DE] Germany .......................... 42 37 334.4

[51] Int. Cl.⁶ .......................... C07H 1/06; C07H 13/06
[52] U.S. Cl. .......................... 536/119; 536/124; 536/127
[58] Field of Search .......................... 536/124, 127, 536/119

[56] References Cited

U.S. PATENT DOCUMENTS

| | | | |
|---|---|---|---|
| 4,814,272 | 3/1989 | Wagner et al. | 536/4.1 |
| 4,933,281 | 6/1990 | Daniels et al. | 536/123 |

FOREIGN PATENT DOCUMENTS

| | | |
|---|---|---|
| 0 282 942 | 9/1988 | European Pat. Off. |
| 314959 | 5/1989 | European Pat. Off. |
| 317036 | 5/1989 | European Pat. Off. |
| 0 153 634 | 8/1989 | European Pat. Off. |
| WO92/05183 | 4/1992 | WIPO |

OTHER PUBLICATIONS

Suzuki et al., "Trehalose Lipid and α–Branched–β–hydroxy Fatty Acid Formed by Bacteria Grown on n–Alkanes," Agric. Biol. Chem., 33:1619–1627 (1969).

Edwards and Hayashi, "Structure of a Rhamnolipid from *Pseudomonas aeruginosa*," Arch. Biochem. Biophys., 111:415–421 (1965).

Mulligan and Gibbs, "Recovery of Biosurfactants by Ultrafiltration," J. Chem. Tech. Biotechnol., 47:23–29 (1990).

Jarvis, F.G., Johnson, M.J., "A Glyco–lipide Produced by *Psuedomonas Aeruginosa*," Amer. Chem. Soc., 71:4124 (1949).

*Primary Examiner*—Douglas W. Robinson
*Assistant Examiner*—Everett White
*Attorney, Agent, or Firm*—Finnegan, Henderson, Farabow, Garrett & Dunner, L.L.P.

[57] ABSTRACT

The invention relates to a process for quantitatively purifying glycolipids, wherein the purification of the glycolipids is effected by acidifying the glycolipid-containing solution to pH $\leq 5.0$, then heating the batch to 60° C.–130° C., and then cooling the batch down to $\leq 50°$ C. and centrifuging it at $\geq 500$ g in order to sediment the glycolipid-containing phase.

10 Claims, No Drawings

PROCESS FOR THE QUANTITATIVE PURIFICATION OF GLYCOLIPIDS

Glycolipids are composed of a fatty acid and a sugar residue. One of the best known glycolipids is trehalose lipid (Suzuki et al., 1969, Agric. Biol. Chem. 33, 1619–1627). It comprises the disaccharide trehalose and two α-branched β-hydroxy fatty acids (crynomycolic acid) which are esterified by hydroxyl groups of the sugar. Glycolipids which contain rhamnose and β-hydroxy fatty acids are described in EP 0 153 634. The rhamnolipid whose structure was the first to be determined comprises two molecules of L-rhamnose and two molecules of β-hydroxydecanoic acid (Ewards and Hayashi, 1965, Arch. Biochem. Biophys., 111, 415–421).

Hitherto known glycolipids have molecular weights between 250 and 2000 Dalton, in each case depending on the sugar and fatty acid moieties. They are, for example, released by bacteria into the surrounding nutrient medium and can accumulate as a mixture of several different glycolipids (EP 0 153 634).

Glycolipids can, for example, be used as emulsifiers, biosurfactants or stabilizers for emulsions.

The processes for purifying glycolipids are based on extraction, crystallization and chromatographic processes (EP 0 282 942; U.S. Pat. No. 4,933,281). However, large quantities of solvents arise in these processes. Mulligan and Gibbs (J. Chem. Tech. Biotechnol. 1990, 47, 23–29) describe an ultrafiltration process for purifying biosurfactants such as surfactin and rhamnolipids. However, the membrane retention capacity described in that publication decreases with increasing pore size. For membranes having a cut-off point of 30,000 Dalton, this leads to glycolipid losses of more than 77%.

Another membrane separation process, in which these losses do not arise, is described in application PCT/EP96/01756, which was published as WO 92/05183. A disadvantage of this process is that permeability decreases with increasing purification and concentration.

Rhamnolipids can also be purified from the culture solution by acidifying the culture solution and subsequently cooling the total batch at about 4° C. for 2 to 3 days (Jarvis, F. G., Johnson, M. J., J. Amer. Chem. Soc. 71, 4124 (1949)).

Daniels et al (U.S. Pat. No. 4,933,281) also purify rhamnolipid from the culture solution by acidifying the culture solution and subsequently cooling the total batch. Example 3 describes how the culture solution is adjusted to pH 2.5 with sulfuric acid and then kept at 4° C. overnight. Following centrifugation, the yield of rhamnolipid is 73%.

It has now been found, surprisingly, that glycolipids can be purified quantitatively by acidifying the glycolipid-containing solution, then heating the total batch, and then, after subsequently cooling the batch, centrifuging it.

The invention consequently relates to a process for quantitatively purifying glycolipids wherein the glycolipids are purified by acidifying the glycolipid-containing solution to pH ≦5.0, subsequently heating the batch to 60° C.–130° C., then cooling the batch to a temperature ≦50° C. and centrifuging the batch to separate off the glycolipid-containing phase.

The invention is described in detail below, in particular in its preferred embodiments.

"Quantitative" denotes that the glycolipid yield is between 90% and 99%, based on the quantity of glycolipid contained in the starting solution.

The definition of the abbreviation "g" is as follows: g=9.80665 m/s$^2$. This value was defined in 1901 by the 3rd conference on weights and measures as the established standard value for acceleration due to gravity.

The process according to the invention can be employed both for purifications on a laboratory scale (milliliter to liter range) and on an industrial scale (cubic meter scale).

Glycolipids can be present in plants or bacteria. The fermentation of microorganisms is preferred for preparing the glycolipids. For this purpose, the microorganisms are cultivated in a manner known per se. The glycolipids secreted into the culture medium are purified quantitatively, once the fermentation is complete, using the process according to the invention.

The process according to the invention is preferably employed for purifying rhamnolipids. The purification of α-L-rhamnopyranosyl-β-hydroxydecanoic acid, 2-O -α-L-rhamnopyranosyl-α-L-rhamnopyranosyl-β-hydroxydecanoic acid, 2-O-α-L-rhamnopyranosyl-α-L-rhamnopyranosyl-β-hydroxydecanoyl -β-hydroxydecanoic acid or α-L-rhamnopyranosyl-β-hydroxydecanoyl-β-hydroxydecanoic acid is particularly preferred.

The process according to the invention comprises the consecutive steps:

1. The glycolipid-containing solution, preferably the culture solution arising from the fermentation of bacteria, is acidified to pH ≦5.0. Preferably, the solution is adjusted to pH 2.5–4.0.

The acidification can be effected with all acids known to the chemist (e.g. $H_2SO_4$, oleum, HCl, $H_3PO_4$, etc.).

Acid in any desired concentration may be used for the process according to the invention. If dilution of the glycolipid-containing solution is undesirable, strongly concentrated acid must, as a consequence, be employed.

The acid is added while stirring the solution and continuously monitoring the pH.

2. Following the acidification, the batch is heated to 60° C.–130° C., preferably 90° C.–110° C. The period required for the heating process can be varied. For example, the heating process can be stopped immediately after reaching the desired maximum temperature.

If pathogenic organisms are contained in the batch, the necessary temperature for inactivating the organisms is maintained until these organisms have been inactivated. It is known to the person skilled in the art which organisms are pathogenic and which temperature and period of time are required for the inactivation.

3. Following the acidification and elevated-temperature steps, the total batch is cooled to ≦50° C., preferably 20° C.–30°C.

The duration of the cooling process is determined by the nature of the cooling (e.g. in a refrigerator in the case of relatively small batches, cooling of large fermenters by way of heat exchangers) and/or the cooling agent used (river water, cooling brine).

Expediently, the cooling process is carried out in such a way that a favorable economic relationship exists between the costs of the energy which is to be employed and the period of the cooling process.

4. In the last step, the batch, which has been cooled down to a temperature of ≦50° C., preferably 20°–30° C., is centrifuged. The centrifugation is effected at ≧500 g until the phases are separated.

Following the centrifugation, the glycolipids are present in the lower phase.

If the process is carried out on a laboratory scale, the lower phase is obtained for further processing simply by pouring off the upper phase.

When the process is carried out on an industrial scale, commercially available separators (e.g. from Westfalia or from Alpha-Laval, Germany) and decanters are employed for separating the phases and thus isolating the glycolipid-containing phase.

The glycolipid yield is between 90%–99%, based on the quantity of glycolipid contained in the starting solution.

That solution which is employed for step 1 of the process according to the invention is designated the starting solution.

Comparative experiments have shown that quantitative purification of glycolipids is not achieved if the glycolipid-containing solution is first heated to 60° C.–130° C. and then, following cooling to room temperature, acidified to pH ≦5.0.

The process according to the invention is used, as already explained above, for the quantitative purification of glycolipids. Naturally, it can also be employed for concentrating them.

As compared with the processes described in the state of the art, the process according to the invention possesses the following advantages:

The process according to the invention is time-saving, since the procedural step, which is described in the state of the art (U.S. Pat. No. 4,933,281), of cooling at 4° C. overnight, i.e. for 12–16 hours, is dispensed with.

The yield is increased from 73%, as described in U.S. Pat. No. 4,933,281, to 90–99%.

When pathogenic organisms are used in the fermentation, the destruction of the organisms, which is legally prescribed in many countries, takes place during the heating procedure of the process according to the invention, consequently saving an additional procedural step which would otherwise be required.

EXAMPLES

Example 1

Batch fermentation on an industrial scale for isolating L-rhamnose a) Preculture A first preculture of the strain *Pseudomonas aeruginosa* DSM 7107 in 4 l of preculture nutrient solution (Tab. 1) is prepared in shaking flasks (2 l Erlenmeyer flasks containing in each case 500 ml of nutrient solution, 30° C., 200 rpm, 20 h). The whole of the first preculture is used for inoculating the second preculture (350 l).

For this, the strain DSM 7107 is fermented aerobically at a temperature of 28° C. for 16 hours in a 450 l fermenter containing 350 l of complex preculture nutrient solution (Table 1) at an aeration rate of 180 l of air/min and at a stirring speed of 300 rpm.

Tab. 1: Preculture nutrient solution:
   10 g/l glucose
   5 g/l casein peptone
   1 g/l yeast extract
   0.5 g/l NaCl.

The whole of the second preculture is used for inoculating the main culture.

b) Main culture 17 m³ of the nutrient solution indicated in Table 2 are prepared in a fermenter possessing a nominal volume of about 30 m³:

Tab. 2: Main culture nutrient solution:
   6.47 g/l 75% strength $H_3PO_4$
   about 8.94 g/l 33% strength NaOH
   0.5 g/l $MgSO_4.7H_2O$
   1 g/l KCl
   15 g/l NaOH
   125 g/l soya bean oil In making up this solution, a pH of 6.8 is established using $H_3PO_4$ and NaOH once the necessary quantity of water has been provided. Once the remaining constituents of the nutrient solution have been added, the pH is corrected to pH 6.2 using $H_2SO_4$.

After sterilizing for 45 minutes, the pH is about 6.3. A solution containing trace elements (Tab. 3) is sterilized in a separate container. For this, the following substances are dissolved in 150 l of deionized water and sterilized:

Tab. 3: Trace element solution:
   2 mg/l sodium citrate.$2H_2O$
   0.28 mg/l $FeCl_3.7H_2O$
   1.4 mg/l $ZnSO_4.7H_2O$
   1.2 mg/l $CoCl_2.6H_2O$
   1.2 mg/l $CuSO_4.5H_2O$
   0.8 mg/l $MnSO_4.1H_2O$
   Deionized water
   The concentration data refer to 1 l of main culture This trace element solution is added to the main fermenter under sterile conditions prior to the inoculation and then 3 further times, i.e. after about 20, 40 and 70 hours of fermentation.

The whole content of the preliminary fermenter (350 l) is used as the inoculum. The fermentation temperature is 30° C. For the first 10 hours of fermentation, the culture is aerated with 250 m³ of air/hour, from the 10th to the 30th hour with 400 m³, and from the 30th hour with 100–75 m³/h.

To control foam, a separate, sterilized silicone defoaming agent VP 1133 (from Wacker) is used which is metered into the fermenter in portions in dependence on the foaming behavior of the fermentation solution and with the aid of a foam electrode.

A radial stirrer possessing four turbines, which have a diameter of 1040 mm, is employed as the stirring element (stirrer φ: fermenter φ=0.4:1). The rate of revolution in the first 10 hours of fermentation is 50 rpm, and from the 10th hour 75 rpm.

About 78 g of rhamnolipids, and a rhamnose content of about 32 g of rhamnose, are produced per liter of culture solution under the abovementioned fermentation conditions in a fermentation of 167 hours duration.

Example 2

Fed-batch fermentation on an industrial scale for obtaining L-rhamnose 18.5 m³ of main culture medium having the composition from Example 1 are inoculated with 350 l of preculture (likewise described in Example 1). The strain *Pseudomonas aeruginosa* DSM 7108 is employed as the production strain. Prior to inoculation, and after 20, 40, 70 and 120 hours of fermentation, a trace element solution (see Example 1) is in each case added under sterile conditions.

The rates of aeration are varied as follows: At the start of fermentation, 250 m³/h, after 10 hours of fermentation, 350 m³/h, and after 30 hours of fermentation, depending on the intensity of foam formation, 100–130 m³ of air/h. Stirring is at 50 rpm for the first 10 hours of fermentation and then at 75 rpm. From the 72nd to the 109th hour of fermentation, a further 564 l of soya bean oil are metered in continuously. Foaming is controlled in the same manner as was described in Example 1. Under the given fermentation conditions, 95 g of rhamnolipids, and a content of rhamnose of 39–40 g, are produced per liter of culture solution in 9 days.

Example 3

50 g of the fermenter solution obtained from Examples 1 or 2 are acidified to pH 3.0 with 6N $H_2SO_4$ and then heated to 100° C. and kept at this temperature for 60 minutes. Subsequently, the solution is cooled down to 20° C. and centrifuged in a laboratory centrifuge for 15 minutes at 3200 g. This centrifugation leads to the formation of two phases which are clearly separated from each other. The lower phase, which has a sedimentation volume of 24% and which is obtained by decanting the upper phase, contains more than 98% of the rhamnolipid mixture contained in the fermentation sample.

Example 4

This example is carried out in an analogous manner to Example 3 with the sole difference that the acidification takes place after the heating.

50 g of the fermenter solution obtained from Example 1 are heated to 100° C. and kept at this temperature for 60 minutes. The solution is then cooled down to 20° C. and adjusted to a pH of 3.0 using 6N $H_2SO_4$. Centrifugation in a laboratory centrifuge (15 minutes at 3200 g) does not lead to any formation of two phases and, as a consequence, the rhamnolipid mixture cannot be separated off.

We claim:

1. A process for quantitatively purifying glycolipids comprising:

acidifying a batch of glycolipid-containing solution to pH lower than or equal to 5.0, subsequently heating the batch to 60° C.–130° C., then cooling the batch to lower than or equal to 50° C. and centrifuging the batch to separate out the glycolipid-containing phase.

2. The process as claimed in claim 1, wherein the glycolipids are rhamnolipids.

3. The process as claimed in claim 2, wherein rhamnolipids are purified from a bacterial culture solution.

4. The process as claimed in claim 2, wherein the rhamnolipids which are purified are selected from a group consisting of α-L-rhamnopyranosyl-β-hydroxydecanoic acid, 2-O-α-L-rhamnopyranosyl-α-L-rhamnopyranosyl-β-hydroxydecanoic acid, 2-O-α-L-rhamnopyranosyl-α-L-rhamnopyranosyl-β-hydroxydecanoyl-β-hydroxydecanoyl-β-hydroxydecanoic acid or α-L-rhamnopyranosyl-β-hydroxydecanoyl-β-hydroxydecanoic acid.

5. The process as in claimed in claim 1, wherein the glycolipid-containing solution is acidified to pH 2.5 to 4.0.

6. The process as claimed in claim 1, wherein the batch is heated to 90° C. to 110° C.

7. The process as claimed in claim 1, wherein the batch is cooled down to 20° C. to 30° C.

8. The process as claimed in claim 1, wherein the batch is centrifuged at greater than or equal to 500 g until the phases are separated.

9. The process as claimed in claim 1, wherein the heating step is maintained for a time sufficient to inactivate any pathogenic organism contained therein.

10. The process as claimed in claim 1 wherein the heating step is stopped immediately after the desired temperature is reached.

* * * * *

UNITED STATES PATENT AND TRADEMARK OFFICE
CERTIFICATE OF CORRECTION

PATENT NO. : 5,656,747
DATED : August 12, 1997
INVENTOR(S) : Johann MIXICH et al.

It is certified that error appears in the above-identified patent and that said Letters Patent is hereby corrected as shown below:

In claim 5, column 6, line 13, after "process as", delete "in".

Signed and Sealed this

First Day of September, 1998

Attest:

Attesting Officer

BRUCE LEHMAN

Commissioner of Patents and Trademarks